United States Patent
Bell

(10) Patent No.: US 6,649,683 B2
(45) Date of Patent: Nov. 18, 2003

(54) SOLID MATRICES FOR SURFACE-ENHANCED RAMAN SPECTROSCOPY

(75) Inventor: Steven Ernest John Bell, Belfast (GB)

(73) Assignee: Avalon Instruments Limited, Belfast (GB)

( * ) Notice: Subject to any disclaimer, the term of this patent is extended or adjusted under 35 U.S.C. 154(b) by 0 days.

(21) Appl. No.: 09/958,225

(22) PCT Filed: Apr. 5, 2000

(86) PCT No.: PCT/GB00/01192
§ 371 (c)(1),
(2), (4) Date: Jan. 11, 2002

(87) PCT Pub. No.: WO00/59624
PCT Pub. Date: Oct. 12, 2000

(65) Prior Publication Data
US 2003/0149153 A1 Aug. 7, 2003

(30) Foreign Application Priority Data
Apr. 6, 1999 (GB) ............................................. 9907688

(51) Int. Cl.[7] .............................. C08J 3/00; C08K 3/08; C08L 29/04
(52) U.S. Cl. .......................... 524/440; 524/31; 524/35; 524/439
(58) Field of Search ................................ 524/439, 440, 524/31, 35

(56) References Cited

U.S. PATENT DOCUMENTS 5,552,086 A 9/1996 Siiman et al. ............ 252/408.1
5,609,907 A 3/1997 Natan ......................... 427/2.12

FOREIGN PATENT DOCUMENTS

GB 1 462 049 1/1977
WO 97/24297 7/1997

OTHER PUBLICATIONS

Ahern et al., "Characterization of Polyacrylamide Gel Formation and Structure by Surface–Enhanced Raman Spectroscopy", Langmuir, vol. 4, No. 5, 1988, pp. 1162–1168.
Siiman et al., "Absorption and Surface–Enhanced Raman Spectra of Silver Organosols in Ethanol", Chemical Physics Letters, vol. 100, No. 2, Sep. 2, 1983, pp. 163–168.
Kurokawa et al., "Functionality of cellulose by impregnation of inorganic substances", Carbohydrate Polymers, vol. 27, No. 4, 1995, pp. 313–320.
Richard L. McCreery, "Raman Spectroscopy for Chemical Analysis", from spectroscopynow.com, 2000, pp. 398–413.

Primary Examiner—Patrick D. Niland
(74) Attorney, Agent, or Firm—Drinker Biddle & Reath LLP

(57) ABSTRACT

A method of forming a solid matrix for use with surface-enhanced Raman spectroscopy is described. The method comprises the steps of: admixing a colloidal metal solution with a polymeric support medium to form a suspension; optionally depositing said suspension on a surface; and then drying the suspension to form the matrix. The polymeric support medium provides a plymer/sol suspension in which the sol particles are resistant to aggregation and precipitation. Upon drying the suspension shrinks to provide a mechanically-hard film subsequently usable to provide a sample for spectroscopic analysis.

34 Claims, 12 Drawing Sheets

Fig. 5

SOLID MATRICES FOR SURFACE-ENHANCED RAMAN SPECTROSCOPY

This application is the U.S. national phase application of PCT International Application No. PCT/GB00/01192 filed Apr. 5, 2000.

The present invention relates to a solid matrix for use with surface-enhanced Raman spectroscopy, and a method of making such a matrix.

Spontaneous Raman scattering from chemical compounds is an inherently weak effect; only a very small proportion of all photons on a normal non-absorbing sample will be Raman scattered. Increased scattering probabilities may be induced by use of the "resonance Raman effect" where the wavelength of the light source is chosen to fall on, or near, an electronic absorbtion band of the sample. However, resonance Raman effects can only be used for samples in which the compound of interest has electronic absorbtion band at one of the excitation wavelengths which are available to the experimenter.

A second method of increasing Raman scattering signals is to use "surface-enhancement" in so-called "surface-enhanced Raman spectroscopy (SERS)". Under conditions where surface and resonance enhancement both operate, the technique is termed "surface-enhanced resonance Raman spectroscopy (SERRS)". Surface-enhancement of Raman signals is observed when the species of interest is absorbed on, or near to, a microscopically-rough metal surface. Not all metals give rise to the effect; the two most commonly-used metals are silver and gold. A very broad range of methods have been used to treat these metals to give surfaces which enhance Raman signals of chemical compounds (ie which are SER(R)S-active). The most widely used are those which involve electrochemical or chemical roughening of metal surfaces, deposition of the metal onto substrate (for example by preparation of metal island films), and preparation of colloidal suspensions of the metals, normally in aqueous solution, hereinafter referred to as sols.

SER(R)S can be an extremely sensitive technique (reports of single molecule detection have been published recently) and has good discrimination because it yields vibrational spectra of compounds which are characteristic of each particular compound. The combination of sensitivity and discrimination makes SER(R)S an obvious technique for the analysis of a very broad range of chemical substances. However, although the potential of the technique is clear, there has been very little exploitation of the technique for routine analytical tasks. The main obstacle to routine analysis is that of signal reproducibility. There are two main sources of this irreproducibility:

1. Irreproducibility in presentation of the sample to the Raman excitation/collection optical system. This is a purely mechanical problem and will not be considered further here.

2. Irreproducibility in the SER(R)S-active surfaces. This is a significant problem. If roughened electrodes are used, the roughening procedure must be exactly replicated between measurements and, even if this is possible, contamination of the surface by highly-scattering compounds is difficult to eliminate. The contamination problem can be removed if a completely fresh surface is used for each measurement. The easiest way to ensure fresh surfaces for measurement is to use small aliquots of colloidal solutions (which are inexpensive to prepare) and then discard them. However, it is widely recognised that preparation of colloidal solutions with identical surface-enhancing properties is extraordinary difficult. Moreover, the solutions themselves are inherently unstable and may decay over time or due to the presence of trace amounts of chemical impurities.

An object of the present invention is to combine the low production cost of colloidal suspensions with the ability to produce large numbers of identical and stable SER(R)S active materials. Moreover, these materials should be presented in forms which are convenient to handle and manipulate but sufficiently inexpensive that they can be used once and then discarded.

According to one aspect of the present invention, there is provided a method of forming a solid matrix for use with surface-enhanced Raman spectroscopy, comprising the steps of:

admixing a colloidal metal solution with a polymeric support medium to form a suspension; and drying the suspension to form the matrix.

The polymeric support medium surrounds the particles in the colloidal metal solution (sol), in effect giving a polymer/sol suspension. When in this form, the sol particles are resistant to aggregation and precipitation, but are still accessible to any solvent-borne analyte. Indeed, it has been found that such suspensions are stable, in that they show no discernable spectral changes over several months.

The term "suspension" as used herein means any solid and/or liquid form of the combination of the components, including gels and emulsions.

Complete drying leaves a mechanically-hard, transparent or translucent film. In the dry films, the metal particles are not only prevented from aggregating, but they are also protected from environmental damage. The films show no discernable change after several months in storage. An inert matrix has been formed from the metal particles and the dry polymeric support medium, although no active bonding has been formed between these substances. Such a matrix can then be used as a support surface for analysis by SER(R)S.

To (re)activate the solid matrix, it can then be treated with an appropriate solvent, or more commonly a solution of analyte, at which point the matrix swells due to solvent ingress and the particles contained within are then free again to interact with the chemical substance to be analysed. Most importantly, the matrix regains its ability to produce surface-enhancement after they have been re-solvated.

Any suitable polymeric support medium may be used in the present invention, which is able to form a suspension with sols formed for use in SER(R)S, and does not reduce their surface enhancement properties. Sols are generally considered to be "unstable", due to the very small particles therein, which are therefore very sensitive to any change, especially any change in environment. The polymeric support medium provides support for the sol metal particles, both in any liquid form, or in any solid form.

Suitable polymeric support media include any known absorbents, or hydrophillic swelling polymers, such as those with carboxylic side chains, including polymers such as polycarbophil, copolymers such as hydroxyethylmethacrylate with methacrylic acid ("HEMA"), polyvinylmethyl maleic anhydride ester, and cellulose-based substances such as hydroxyethylcellulose.

The polymeric support medium may be solid or liquid.

Where the polymeric support medium is wholly or substantially a liquid or gel, etc, ie the suspension formed is at least not a solid, the suspension is applied or deposited on a surface, e.g. spread across a support, and then dried in air or under a vacuum, etc. During the drying, the polymer/sol suspension shrinks as the polymeric support medium returns to an anhydrous state.

The surfaces on which the polymer/sol suspension can be applied to include any form, design or shape. One common form is a flat plate, generally of clear glass. Alternatively, the suspension could be applied to multiple plates or wells, eg. a (standard) microwell plate. The suspension could also be added to eg the inside of capillary tubes or pipettes, which tubes or pipettes can be used to draw up very small samples of analyte directly.

Preferably, any liquid suspension has at least some viscosity, to make easier its application onto a surface. A gel suspension can generally be readily screened onto a surface.

Where the polymeric support medium is wholly or substantially a solid, e.g. a more cross-linked carboxylic hydrophillic polymer or copolymer such as HEMA, the colloidal metal solution can be added directly thereto to form the suspension. The support medium may swell, but will return to size once the suspension is dried, e.g. in air or under vacuum, etc. Such support media could be provided in sheet form, which could be divided into a plurality of suitable matrices, (each one for subsequent repeatable analysis), once the colloidal metal solution is absorbed or suspended thereby.

Whilst any metal particles that could be used in Raman spectroscopy could be used in the colloidal metal solution of the present invention, such metal particles are generally either silver or gold.

According to a second aspect of the present invention, there is provided a solid matrix for use with surface-enhanced Raman spectroscopy, which matrix includes metal particles and polymeric support medium, preferably as a thin film.

Preferably, the solid matrix is a flat sheet or film or is located on a flat surface such as a plate, or on a single or multiple well plate.

The present invention clearly provides the ability to prepare a number of identical and stable SER(R)S active support surfaces, which can be stored over a relatively long term, and which can provide an active medium for use at any time, and whose variation should be sufficiently minimal as to wholly or substantially provide similar Raman spectra from the same analyte. Reproducibility of spectra is therefore now possible over much longer time periods than before, and a lot less time and effort should be involved in having to try and replicate the analyte support conditions each time a Raman spectrum is desired.

It is considered that the present invention could allow the use of Raman spectroscopy to be used much more quickly and more widespread than before, eg outside forensic laboratories, and much closer to the source of analytes. Its' local use in forensics and/or medical is diagnostics is clearly possible.

Embodiments of the present invention will now be described by way of example only, and in relation to the accompanying drawings in which;

Figure 5:
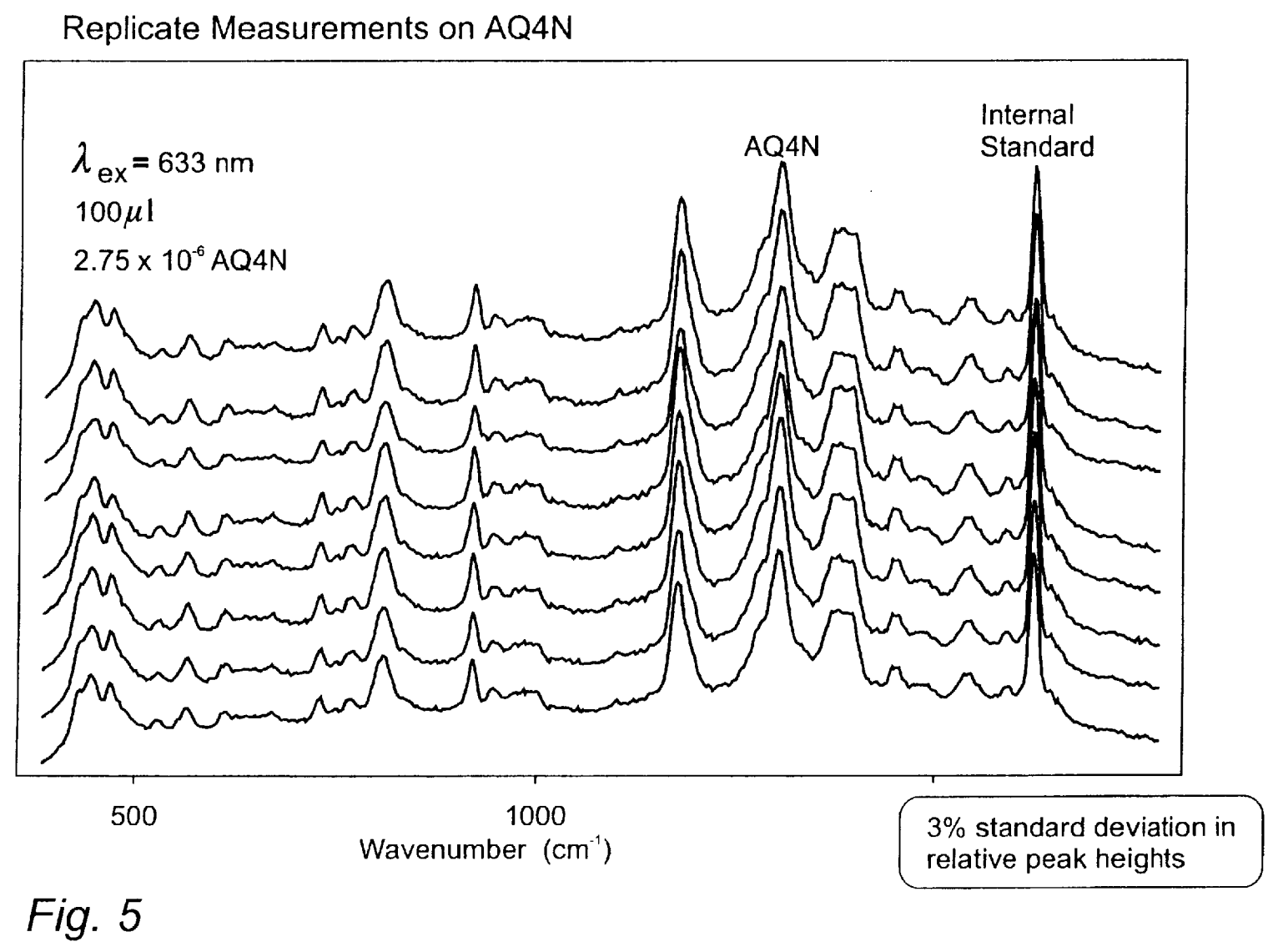

FIG. 5 is replicate measurements of the surface-enhanced Raman spectra of the putative anti-cancer drug AQ4N taken from eight different Noveon/silver films. Internal standard was crystal violet.

MATERIAL AND METHODS

Figure 1A:
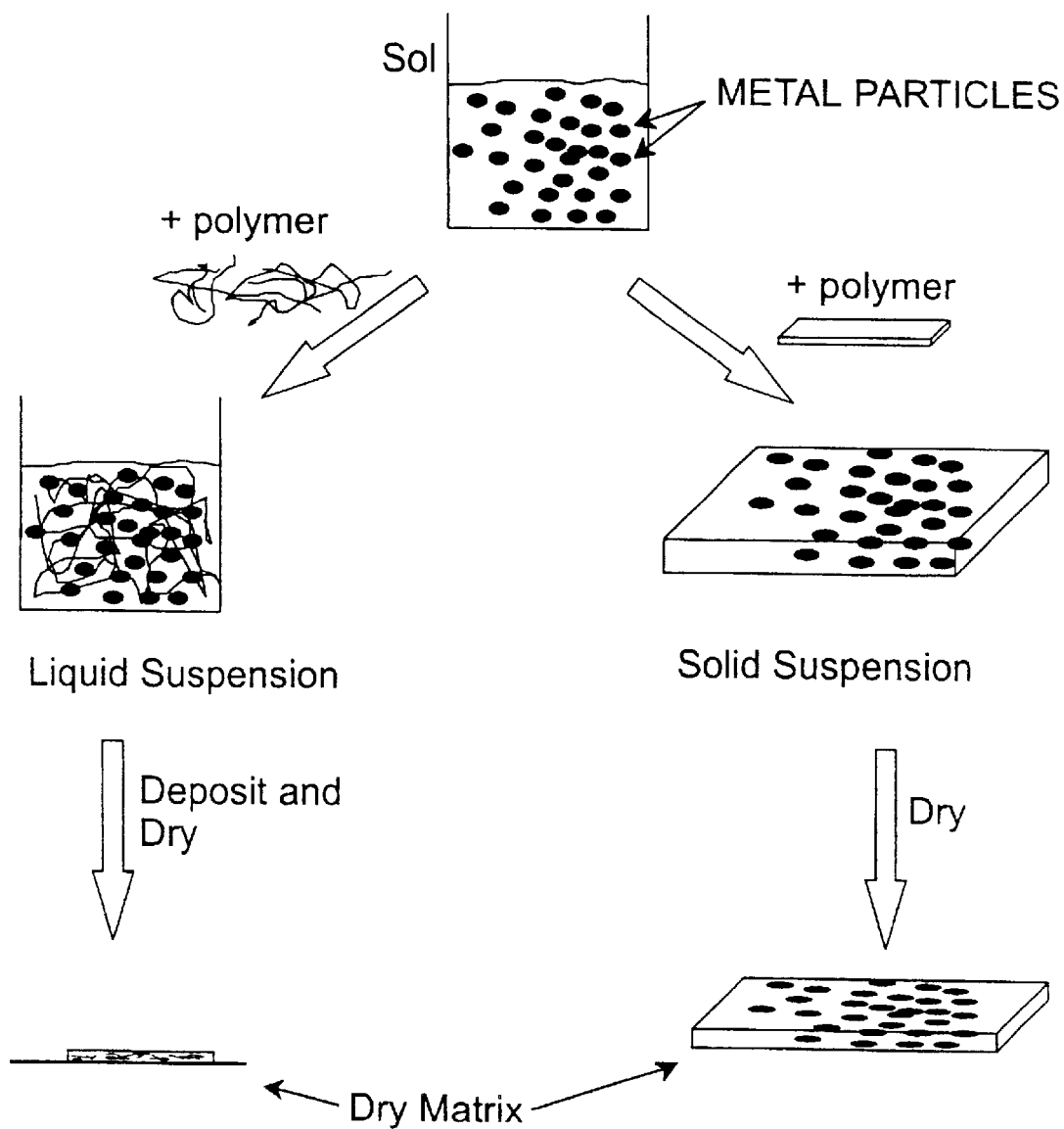
FIG. 1a is a schematic drawing of two methods of forming a solid matrix according to the present invention.

Aqueous silver and gold sols as shown in FIG. 1a were prepared by standard literature methods and were either used directly or were concentrated by centrifugation, using previously reported methods.

In one arrangement, viscous polymer/sol solutions were then prepared by addition of one of the liquid hydrophillic swelling polymers (see below) to the aqueous sol, as shown in the left part of FIG. 1a. The mixture was allowed to stand for several hours with occasional stirring, to allow hydration of the polymer, before a final, thorough mixing stage. The viscosity of the polymer/sol solutions can be varied simply by altering the concentration of polymer in the solution.

Figure 1B:
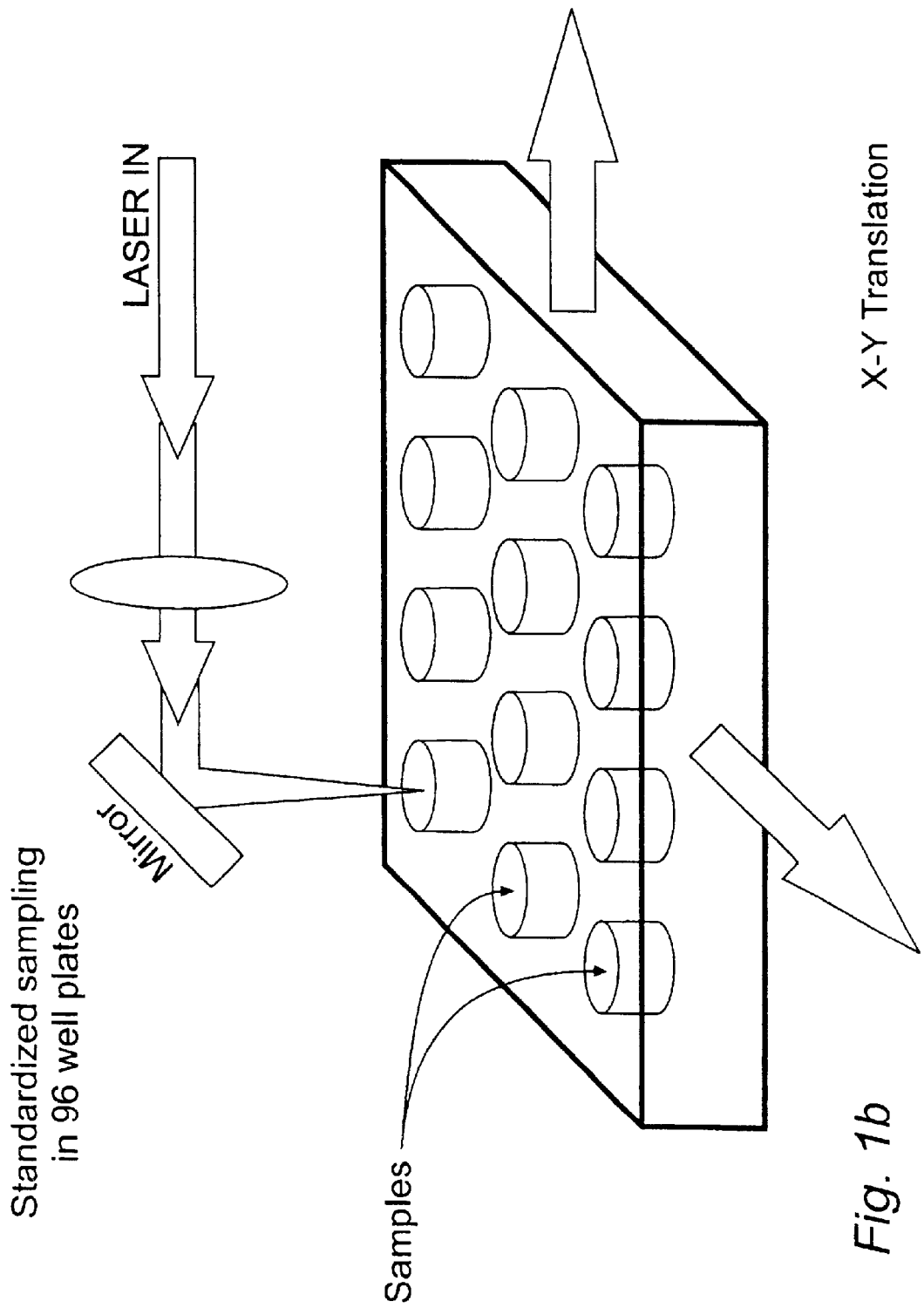
FIG. 1b is a standardised sampling arrangement in multiwell plates. Each well in the plate contains a dried polymer/sol matrix according to the present invention which is activated by addition of the analyte in solution.
Figure 2:
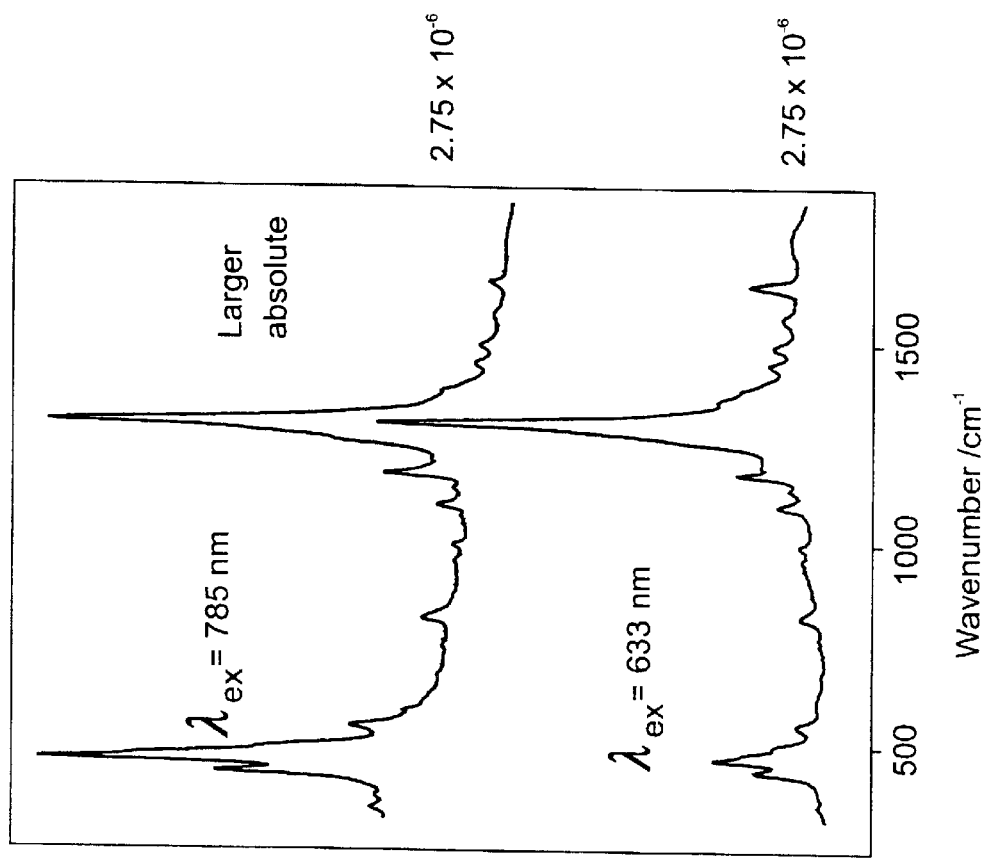
FIG. 2 is surface-enhanced Raman spectra of the putative anti-cancer drug AQ4N taken at two different excitation wavelengths in Noveon/silver films.
Figure 2:
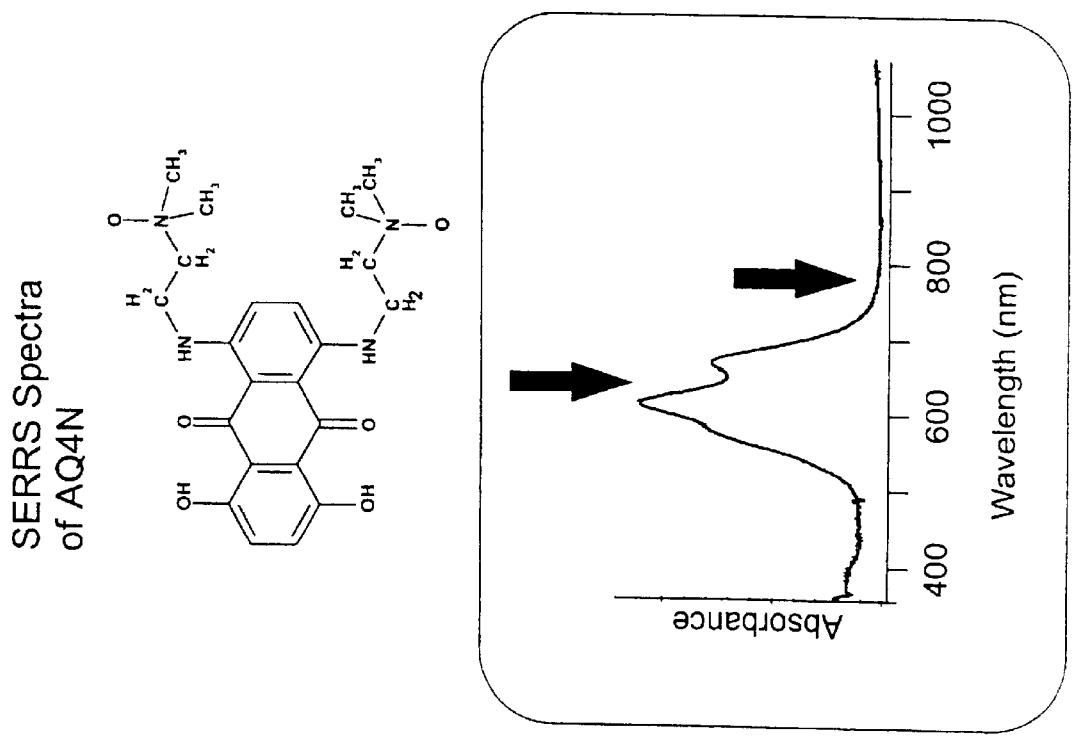
Figure 3:
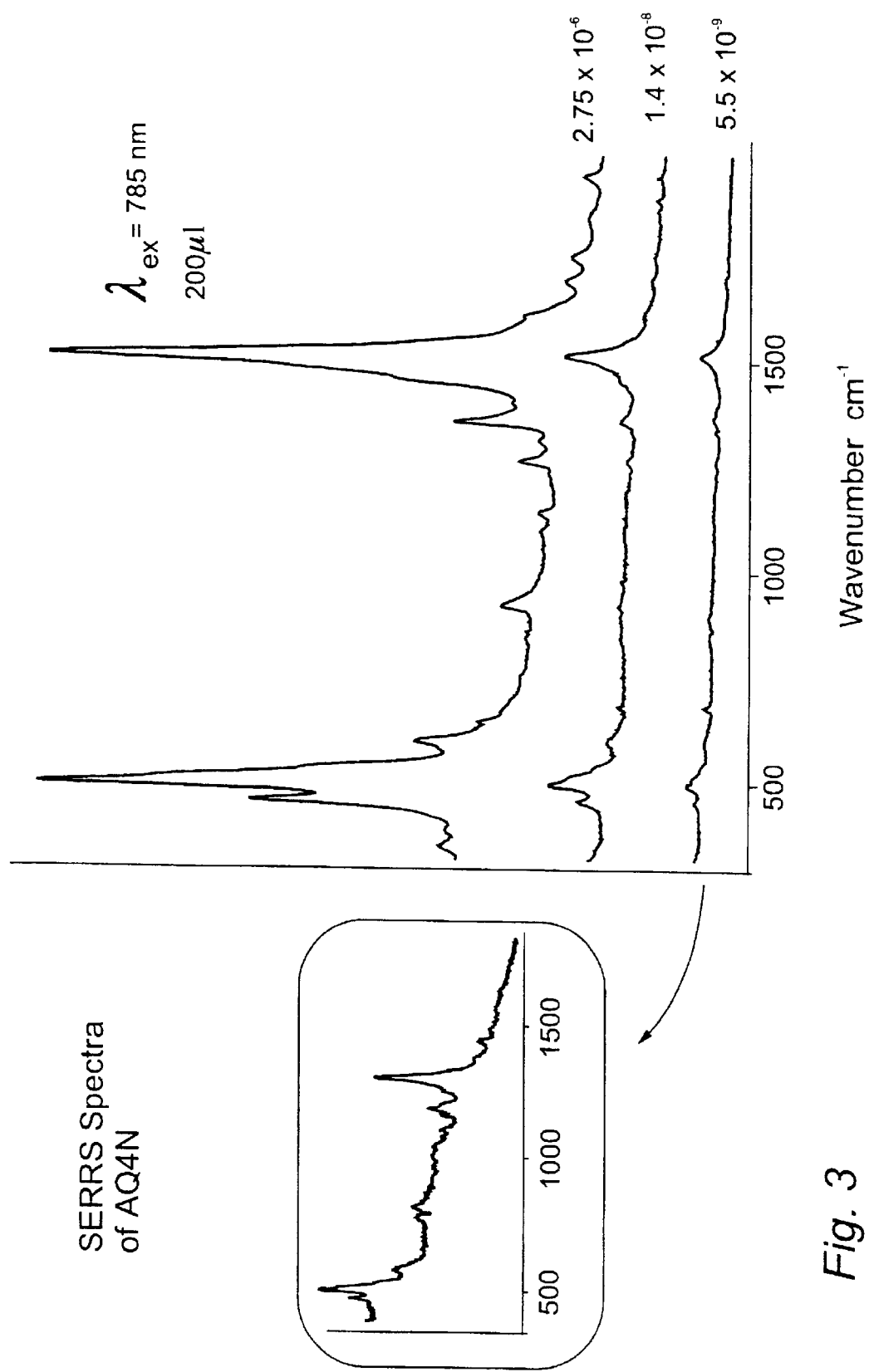
FIG. 3 is surface-enhanced Raman spectra of the putative anti-cancer drug AQ4N taken over a 500× concentration range in Noveon/silver films.
Figure 4:
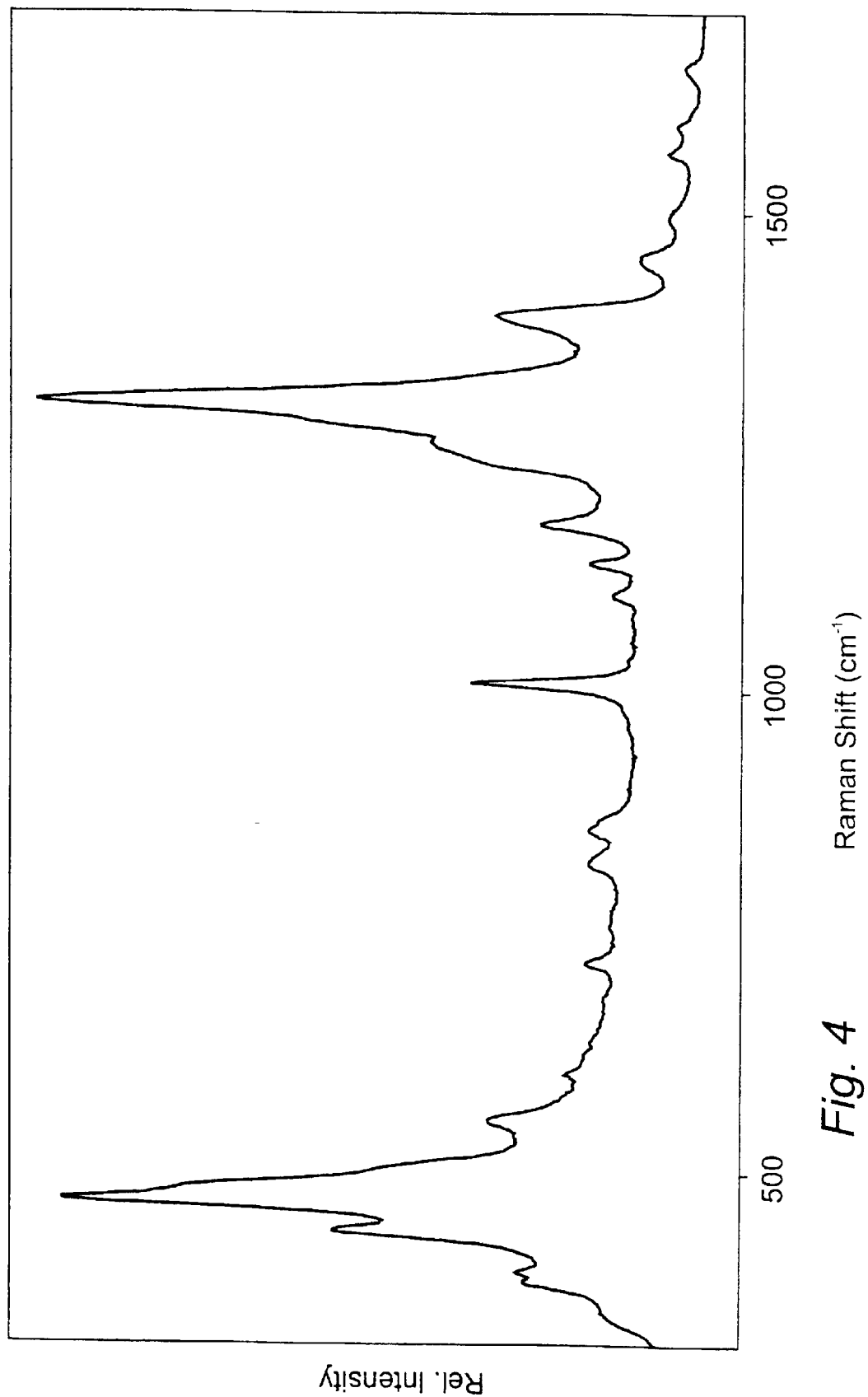
FIG. 4 is surface-enhanced Raman spectra of the putative anti-cancer drug AQ4N taken in a Gantrez/silver film.
Figure 6:
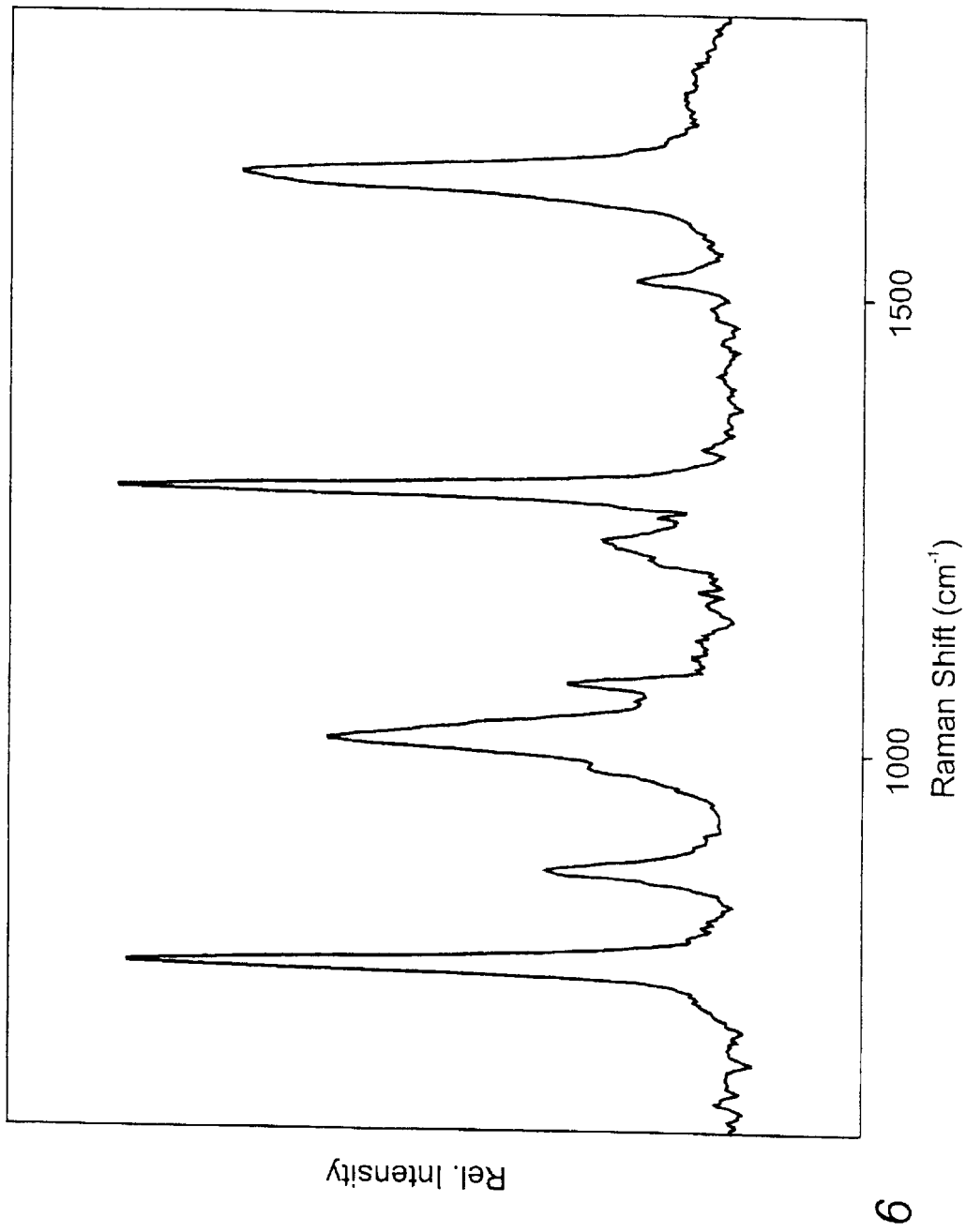
FIGS. 6–11 are surface-enhanced Raman spectra (taken in Noveon/silver films) of a range of chemically distinct compounds, illustrating the range of compounds which this invention can be applied to and the range in excitation wavelengths which have already been used.
Figure 7:
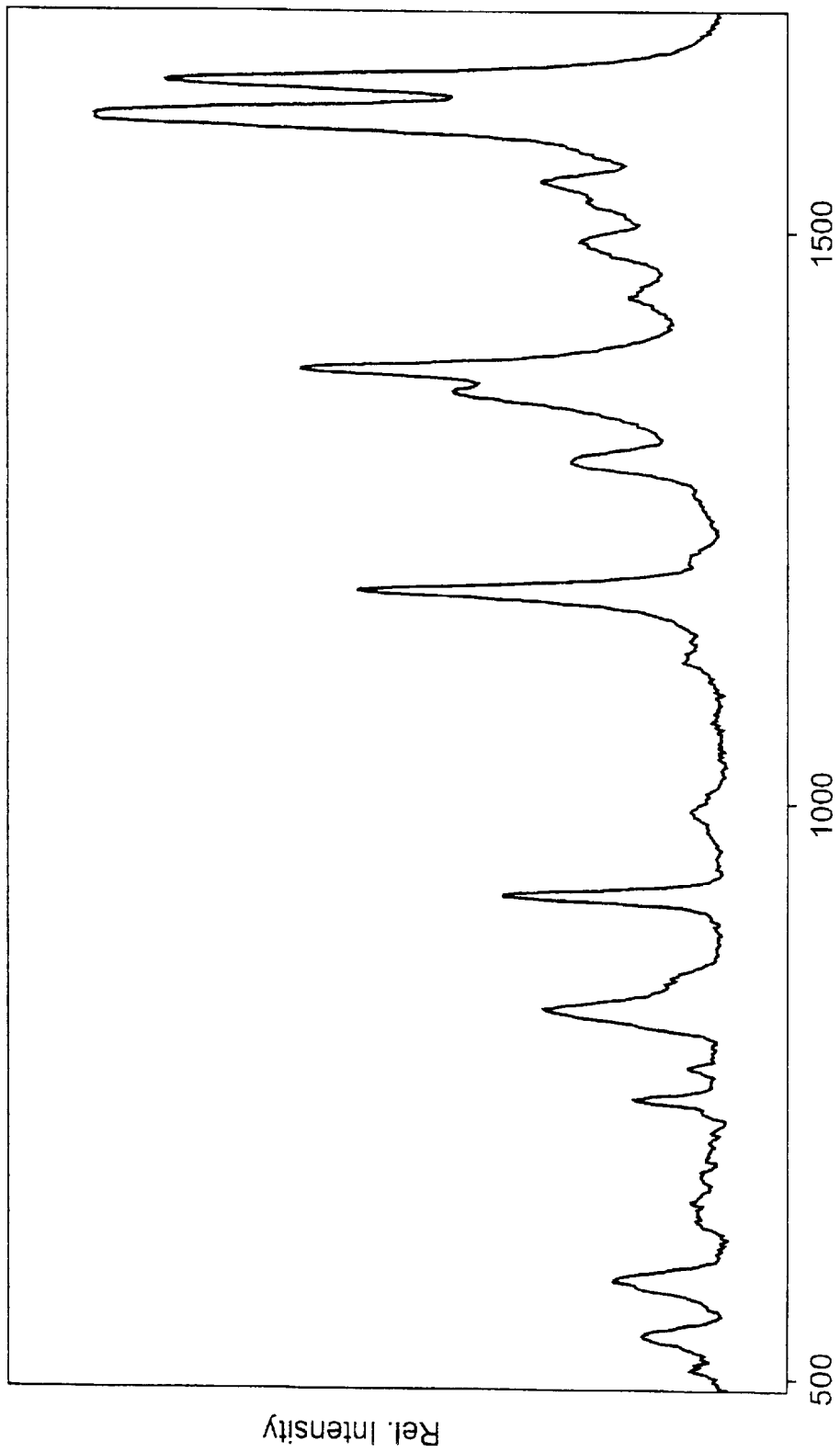
Figure 8:
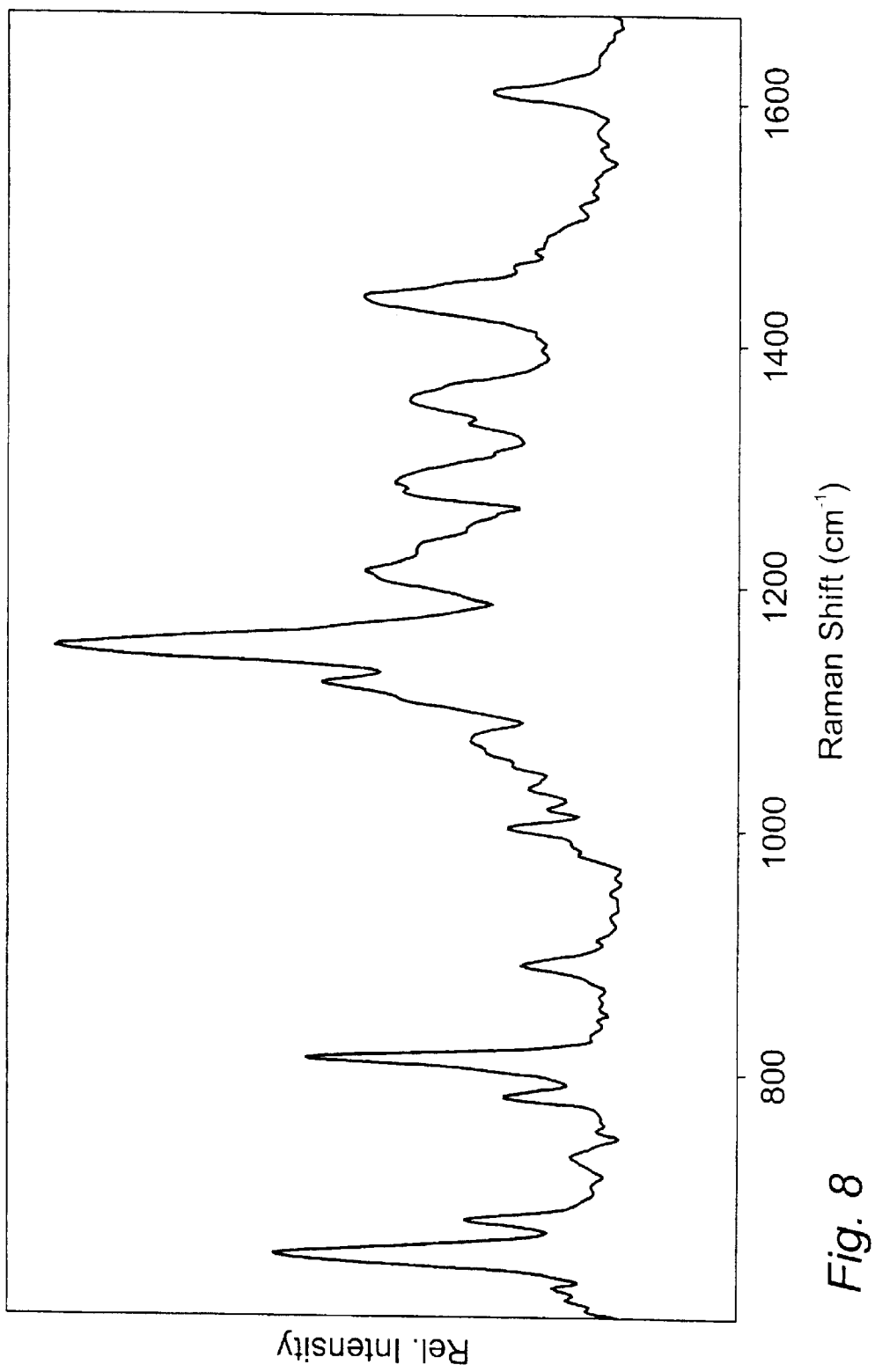
Figure 9:
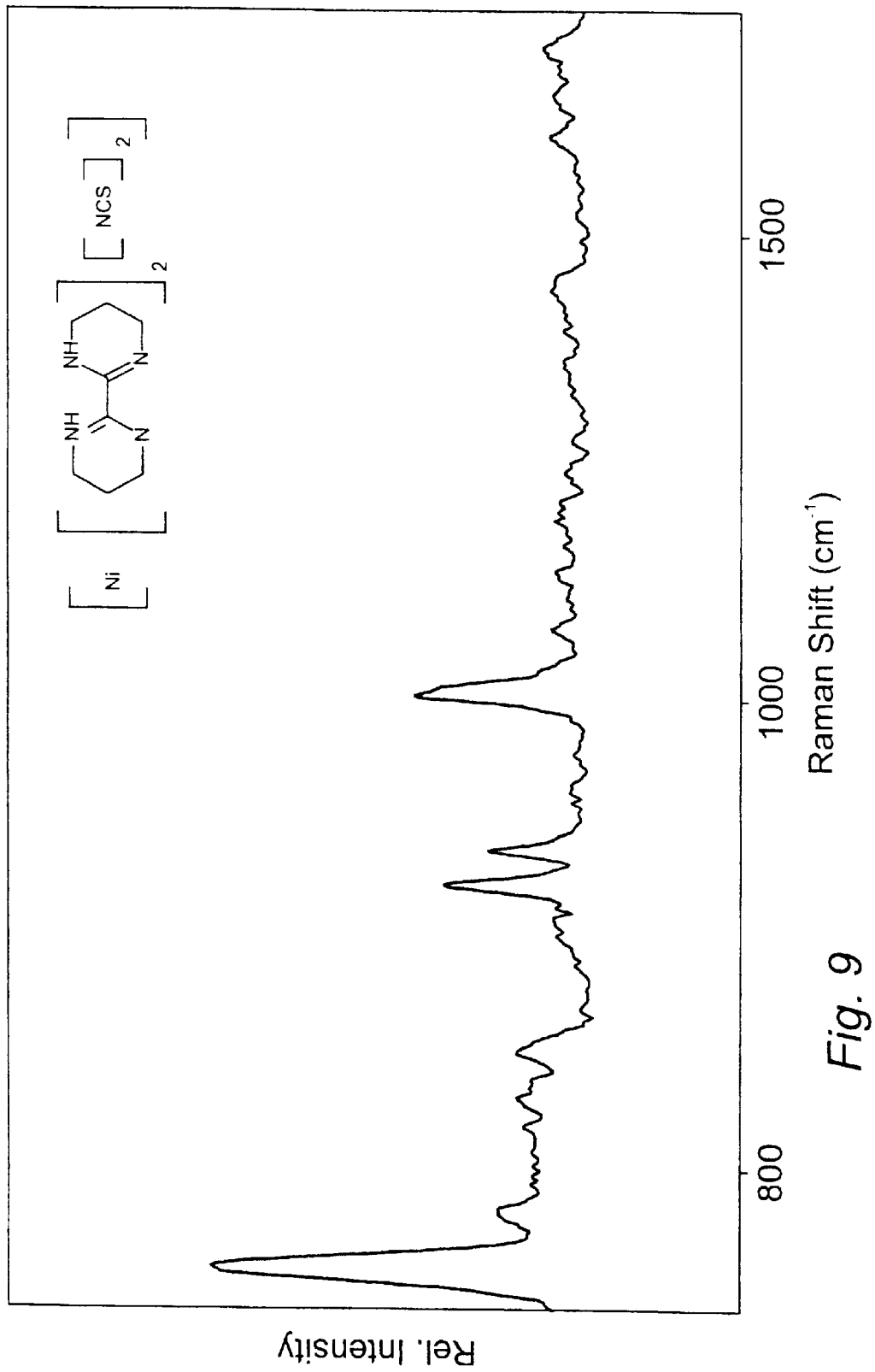
Figure 10:
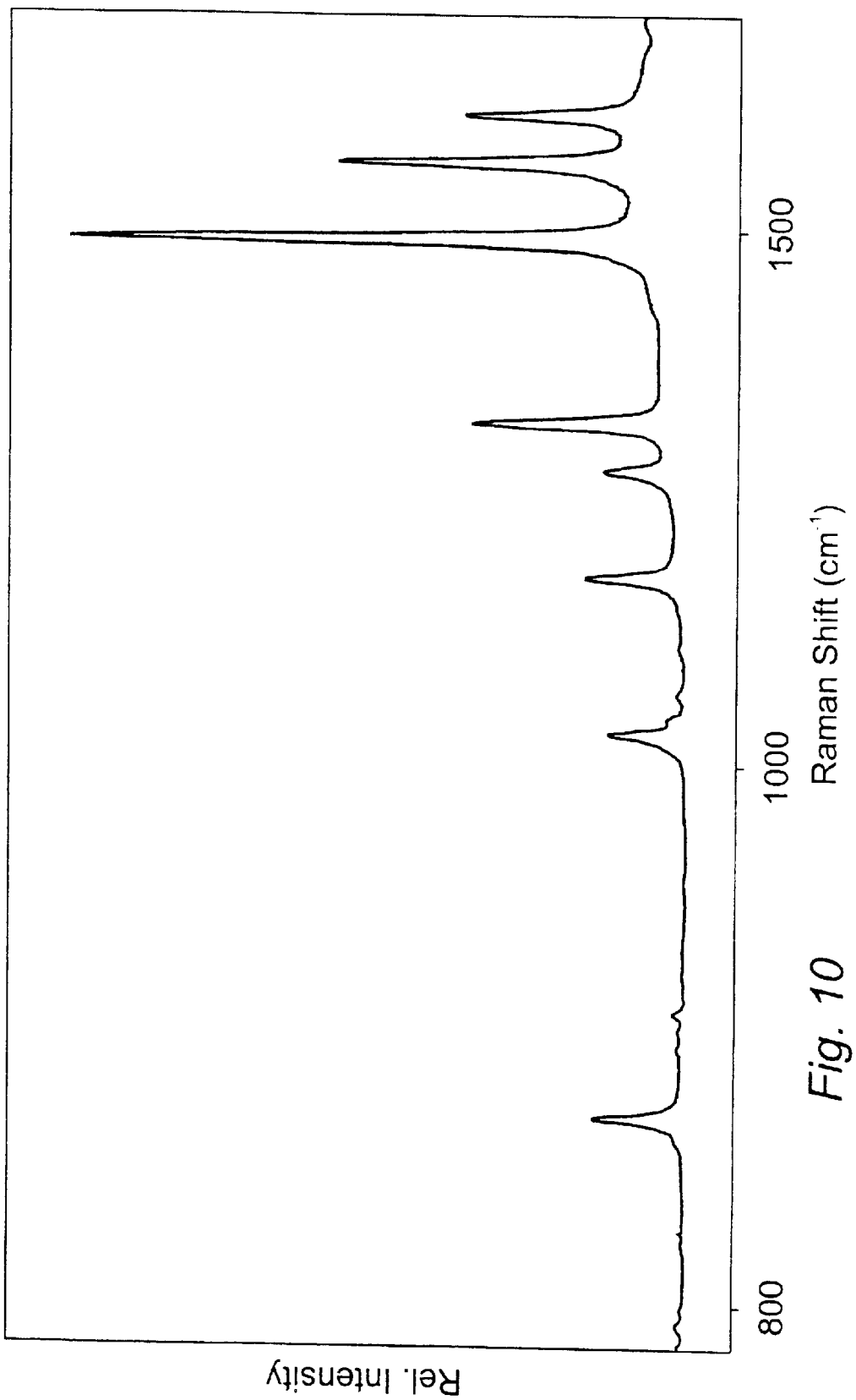
Figure 11:
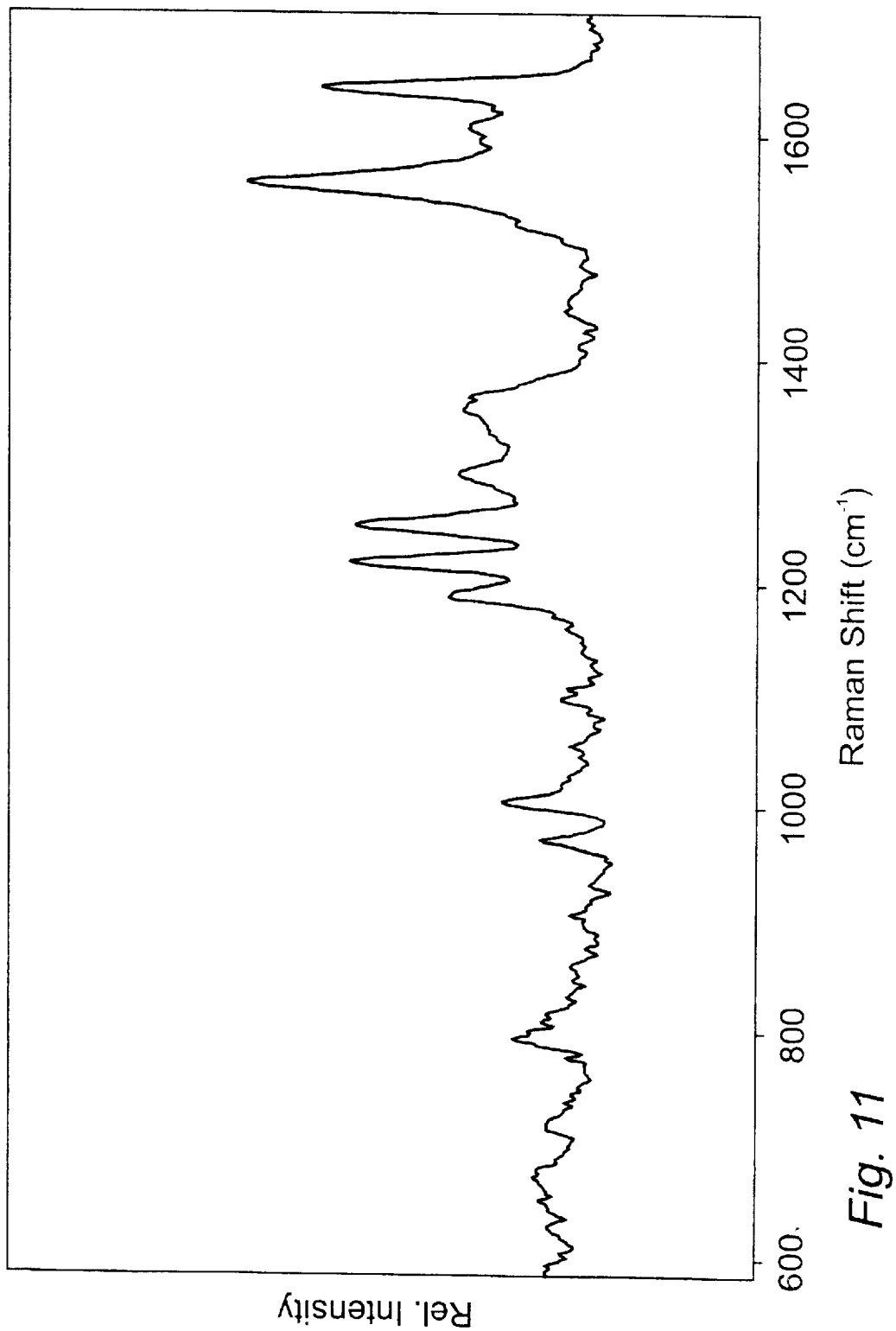

The liquid or gel polymer/sol solution was then deposited onto one of a number of different substrates including; metallic, plastic, glass and quartz supports (e.g. flat glass plate as shown in FIG. 1a), the wells of micro-well plates (as shown in FIG. 1b), the inner surfaces of hollow capillary tubes and on the tips of optical fibres. The deposited layers were then dried to a film (drying times depended on layer thickness and ranged from 2 hours for layers <100 $\mu$m thick, to two days for layers—5 mm thick). The dried films were stored in a desiccated environment. Alternatively, after drying, the films could be scraped from the support and then powdered. When this powder was re-dissolved it formed a SER(R)S-active solution.

In another arrangement, and as shown in the right part of FIG. 1a, the sol was added directly to a solid hydrophillic swelling polymer such as HEMA to form a solid suspension. This was dried to give a solid matrix, which was also stored in a desiccated environment before use. When this matrix was brought into contact with an aqueous solution of analyte, it was found to be SER(R)S active.

The solid hydrophillic swelling polymer could be divided either prior to or after addition of the sol, to provide a number of wholly or substantially identical solid matrices for repeatable performance in use from the same sol. Similarly, a number of depositions could be made from a liquid suspension to provide a number of matrices simultaneously, or a solid matrix formed thereby could be subsequently subdivided. Thus, large numbers of identical and stable solid matrices can be formed with ease.

Raman spectra were recorded using 458, 488, 514, 633 or 785 nm excitation (Spectra-Physics 2020 Ar$^+$ laser or Spectra-Physics Ti/sapphire laser pumped by a Spectra-Physics 2020 Ar$^+$ laser, typically 10–100 mw at sample) using a 180° backscattering geometry. Scattered light was collected, passed through a Kaiser Optical System holographic notch filter and then dispersed by a Jobin-Yvon HR640 single stage spectrograph onto a Princeton Instruments LN1152 liquid $N_2$ CCD detector. Spectra were typically accumulated for 120s and were exported to the "Lab-Calc" spectral manipulation package for processing and presentation. The spectrometer was calibrated using a standard 50/50 mixture of toluene and acetonitrile.

Results

The Raman signals obtained from the polymer/sol matrices (either before of after drying/rehydration) were of comparable intensity to those obtained from the simple sols to which the same analytes had been added. Raman signals due to the polymer support medium gave negligible interference and there was no significant increase in background luminescence intensity. The rehydrated films acted in just the same way as the more conventional sols form which they were prepared. There is no reason to believe that the range of analytes which can be studied by conventional SER(R)S cannot also be studied using polymer/sol systems described herein.

To demonstrate this point, signals were recorded from a broad cross-section of chemical compounds over the wavelength range 457.9–785 nm. It would be an enormous task to record exemplars from every class of compound which the polymer/sol combinations could be used to study, or even to duplicate the enormous range of compounds which have already been studied using conventional SER(R)S. However, spectra of a number of samples enhanced through the SER(R)S-active films described above are shown herewith. The samples encompass porphyrins, azo dyes, indicators, metal complexes and therapeutic drugs. Spectra from the centre and two extremes of the wavelength range investigated are shown.

The spectra herewith were, in the main, obtained from films prepared via a liquid suspension, with a cross-linked polyacrylic acid (polycarbophil, trade name Noveon AA1 from B. F. Goodrich), but an example obtained from a polyvinylmethyl ester of maleic anhydride (trade name Gantrez, I.S.P Ltd) is also shown. There are many polymers available under various trade names, which are similar to the above. They are extensively used in pharmaceutical, cosmetic and cleansing products. The polymers available commercially, (even a single manufacturer may produce a complete series), differ in the Theological properties, since they are crossed-linked differently or have slightly different polymer backbones.

The spectra herewith also shows data taken of a single exemplar, the putative anti-cancer drug AQ4N, over a broad concentration range and at two different excitation wavelengths. The reproducibility of the films formed is also illustrated. Shown herein are replicate spectra of a sample of AQ4N, the spectra are of small aliquots of the sample which were added to different dehydrated films. The spectra were normalised by addition of an internal standard. Under these conditions even crude quantitative analysis (ratioing the peak heights of the strongest band in the sample and standard) shows only a very small 3% variation over the sample set taken.

What is claimed is:

1. A method of forming a solid matrix for use with surface-enhanced Raman spectroscopy, comprising the steps of:
   admixing a colloidal metal solution with a hydrophilic polymeric support medium to form a suspension; and drying the suspension to form the matrix.

2. A method as claimed in claim 1 wherein the polymeric support medium is an absorbant.

3. A method as claimed in claim 1 wherein the polymeric support medium is a hydrophillic polymer with carboxylic side chains.

4. A method as claimed in claim 1 wherein the suspension is deposited on a surface prior to drying.

5. A method as claimed in claim 4 wherein the surface is selected from the group comprising plates, wells, tubes, pipettes and optical fibres.

6. A method as claimed in claim 4 wherein the surface is wholly or substantially formed of a material selected from the group comprising glass, plastic, metal and quartz.

7. A method as claimed in claim 4 wherein the surface is a microwell plate.

8. A method as claimed in claim 4 wherein the surface is the inside of a capillary tube or pipette.

9. A method as claimed in claim 4 wherein the polymeric support medium is polycarbophil or polyvinylmethyl maleic anhydride ester.

10. A method as claimed in claim 4 wherein the polymeric support medium is a cellulose-based substance.

11. A method as claimed in claim 10 wherein the cellulose-based substance is hydroxyethylcellulose.

12. A method as claimed in claim 4 wherein a viscous suspension is formed.

13. A method as claimed in claim 1 wherein the suspension is wholly or substantially a solid.

14. A method as claimed in claim 12 wherein the polymeric support medium is a thin film or sheet.

15. A method as claimed in claim 13 wherein the polymeric support medium is a copolymer of hydroxyethylmethacrylate and methacrylic acid.

16. A method as claimed in claim 1 wherein the metal in the metal solution is silver or gold.

17. A method as claimed in claim 1 wherein the solid matrix is subsequently powdered.

18. A solid matrix for use with surface-enhanced Raman spectroscopy, which matrix includes metal particles and a hydrophilic polymeric support medium.

19. A solid matrix as claimed in claim 18 wherein the matrix is a thin film.

20. A solid matrix as claimed in claim 18 wherein the solid matrix is supported on a flat surface.

21. A solid matrix as claimed in claim 19 wherein the matrix is supported on a well plate.

22. A solid matrix as claimed in claim 18 wherein the metal particles are silver or gold.

23. A solid matrix as claimed in claim 18 wherein the polymeric support medium is an absorbant.

24. A solid matrix as claimed in claim 18 wherein the polymeric support medium is a hydrophillic polymer with carboxylic side chains.

25. A solid matrix as claimed in claim 18 wherein the polymeric support medium is selected from the group comprising polycarbophil, hydroxyethylcellulose, HEMA, or polyvinylmethyl maleic anhydric ester.

26. A solid matrix as claimed in claim 18 wherein the matrix is a powder.

27. A solid matrix as claimed in claim 18 for use with surface-enhanced resonance raman spectroscopy.

28. A solid matrix as claimed in claim 18 whenever prepared by forming a solid matrix for use with surface-enhanced Raman spectroscopy, comprising the steps of:
   admixing a colloidal metal solution with a polymeric support medium to form a suspension; and drying the suspension to form the matrix.

29. A method of preparing a sample for analysis by surface-enhanced Raman spectroscopy, comprising the steps of:
   providing a solid matrix for use with surface-enhanced Raman spectroscopy, which matrix includes metal particles and a hydrophilic polymeric support medium; and adding a solvent to the matrix.

30. The use of a solid matrix as claimed in claim 29 wherein the solid matrix is prepared for analysis by treatment with a solvent.

31. A method as claimed in claim 29 wherein the solvent is an analyte.

32. A method as claimed in claim 29 wherein the surface-enhanced Raman spectroscopy is surface-enhanced resonance Raman spectroscopy.

33. A method of forming a suspension for use with surface-enhanced Raman spectroscopy, comprising the step of:

admixing a colloidal metal solution with a polymeric support medium to form the suspension.

34. A suspension for use with surface-enhanced Raman spectroscopy, which suspension includes metal particles and a polymeric support medium.

* * * * *